United States Patent [19]

Tjoeng et al.

[11] Patent Number: 4,879,313
[45] Date of Patent: Nov. 7, 1989

[54] NOVEL PLATELET-AGGREGATION INHIBITORS

[75] Inventors: Foe S. Tjoeng, Manchester; Steven P. Adams, St. Charles, both of Mo.

[73] Assignee: Mosanto Company, St. Louis, Mo.

[21] Appl. No.: 221,703

[22] Filed: Jul. 20, 1988

[51] Int. Cl.$^4$ ............................................. A61K 31/21
[52] U.S. Cl. ..................................... 514/616; 514/20; 564/153; 530/331; 530/332
[58] Field of Search .................. 514/616, 20; 564/153, 564/157; 530/331, 332

[56] References Cited

U.S. PATENT DOCUMENTS

| | | | |
|---|---|---|---|
| 4,051,141 | 9/1977 | Castaigne | 260/294.8 |
| 4,127,580 | 11/1978 | Braye | 546/114 |
| 4,517,686 | 5/1985 | Ruoslahti et al. | 3/1 |
| 4,578,079 | 3/1986 | Ruoslahti et al. | 623/11 |
| 4,589,881 | 5/1986 | Pierschbacher et al. | 623/11 |
| 4,614,517 | 9/1986 | Ruoslahti et al. | 623/11 |
| 4,661,111 | 4/1987 | Ruoslahti et al. | 623/11 |
| 4,683,291 | 7/1987 | Zimmerman et al. | 530/324 |

OTHER PUBLICATIONS

Kloczewiak et al. Biochem. 23, 1767–1774 (1984).
Plow et al., Proc. Natl. Acad. Sci. 82, 8057–8061 (1985).
Ruggeri et al., Ibid. 83, 5708–5712 (1986).
Ginsberg et al., J. Biol. Chem. 260(7), 3931–3936 (1985).
Haverstick et al., Blood 66(4) 946–952 (1985).

*Primary Examiner*—Frederick Waddell
*Attorney, Agent, or Firm*—Scott J. Meyer; James W. Williams, Jr.

[57] ABSTRACT

Novel peptide mimetic compounds are provided which have useful activity as inhibitors of platelet aggregation. These compounds have the chemical structure

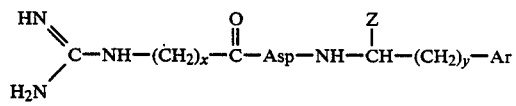

wherein
x=6 to 10,
y=0 to 4,
Z=H, COOH, CONH$_2$ or C$_{1-6}$ alkyl,
Ar=phenyl, biphenyl or napthyl, each substituted with 1 to 3 methoxy groups, or an unsubstituted phenyl, biphenyl, napthyl, pyridyl or thienyl group, and
Asp=aspartic acid residue.

10 Claims, No Drawings

NOVEL PLATELET-AGGREGATION INHIBITORS

BACKGROUND OF THE INVENTION

This invention relates to novel peptide mimetic compounds having activity as inhibitors of platelet aggregation.

Fibrinogen is a glycoprotein present as a normal component of blood plasma. It participates in platelet aggregation and fibrin formation in the blood clotting mechanism.

Platelets are cellular elements found in whole blood which also participate in blood coagulation. Fibrinogen binding to platelets is important to normal platelet function in the blood coagulation mechanism. When a blood vessel receives an injury, the platelets binding to fibrinogen will initiate aggregation and form a thrombus. Interaction of fibrinogen with platelets occurs through a membrane glycoprotein complex, known as gpIIb-/IIIa; this is an important feature of the platelet function. Inhibitors of this interaction are useful in modulating platelet thrombus formation.

It is also known that another large glycoprotein named fibronectin, which is a major extracellular matrix protein, interacts with fibrinogen and fibrin, and with other structural molecules such as actin, collagen and proteoglycans. Various relatively large polypeptide fragments in the cell-binding domain of fibronectin have been found to have cell-attachment activity. See U.S. Pat. Nos. 4,517,686; 4,589,881; and 4,661,111. These polypeptides include an internal amino acid sequence Arg-Gly-Asp-Ser. Certain relatively short peptide fragments from the same molecule were found to promote cell attachment to a substrate when immobilized on the substrate or to inhibit attachment when in a solubilized or suspended form. See U.S. Pat. Nos. 4,578,079 and 4,614,517. These peptides were defined as X-Arg-Gly-Asp-R-Y wherein
X=H or amino acid,
R=Thr or Cys;
and X-Arg-Gly-Asp-Ser-Y wherein
X=H or amino acid,
Y=OH or amino acid.

In U.S. Pat. No. 4,683,291, inhibition of platelet function is disclosed with synthetic peptides designed to be high affinity antagonists of fibrinogen binding to platelets. These synthetic peptides have up to 16 amino acid residues with Arg-Gly-Asp-Va or Arg-Gly-Asp-Ser at the C-terminal.

Similar synthetic peptides which contain the Arg-Gly-Asp sequence and their use as inhibitors of fibrinogen binding to platelets are disclosed by Koczewiak et al., *Biochem.* 23, 1767–1774 (1984); Plow et al., *Proc. Natl. Acad. Sci.* 82, 8057–8061 (1985); Ruggeri et al., *Ibid.* 83, 5708–5712 (1986); Ginsberg et al., *J. Biol. Chem.* 260 (7), 3931–3936 (1985); and Haverstick et al., *Blood* 66 (4), 946–952 (1985).

In co-pending application Ser. No. 128,379 filed Dec. 3, 1987, certain novel tetrapeptide derivatives are disclosed which have enhanced activity as inhibitors of platelet aggregation. These tetrapeptide derivatives contain the sequence X-Gly-Asp-Y in which X and Y are defined to comprise a variety of organic moieties. An illustrative preferred example is Arg-Gly-Asp-(O-methyl-Tyr)-NH$_2$.

BRIEF DESCRIPTION OF THE INVENTION

In accordance with the present invention, novel peptide mimetic compounds are provided which have useful activity as inhibitors of platelet aggregation. They are believed to act by antagonizing interactions between fibrinogen and/or extracellular matrix proteins and the platelet gpIIb/IIIa receptor. These novel inhibitor compounds can be represented by the following chemical structure:

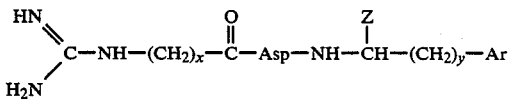

wherein
x=6 to 10,
y=0 to 4,
Z=H, COOH, CONH$_2$ or C$_{1-6}$alkyl,
Ar=phenyl, biphenyl or napthyl, each substituted with 1 to 3 methoxy groups, or an unsubstituted phenyl, biphenyl, napthyl, pyridyl or thienyl group, and
Asp=aspartic acid residue.

In a preferred group of the novel peptide mimetic compounds, x=7 to 8.

When compared structurally with the Arg-Gly-Asp-(O-methyl-Tyr)-NH$_2$ and other tetrapeptide derivatives of co-pending application Ser. No. 128,379, it will be seen that in the present compounds a peptide bond

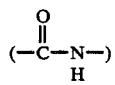

is replaced with a pseudopeptide or peptide mimetic bond (—CH$_2$—CH$_2$—). Thus, in an illustrative preferred compound of the above group in which x=7, y=1, Z=H and Ar=p-methoxyphenyl, namely 8-guanidino-octanoyl-Asp-2-(4-methoxyphenyl)-ethylamide, the amide bond between the N-terminal residue and the glycine residue, is replaced with a pseudopeptide bond.

The novel inhibitor compounds of this invention are more resistant to proteolysis than the prior inhibitors without the pseudopeptide bond and thus have longer duration of activity. These novel compounds are active inhibitors of platelet aggregation. In an in vivo thrombocytopenia assay, the preferred 8-guanidino-octanoyl-Asp-2-(4-methoxyphenyl)ethylamide was active at an effective dose of about one eighth the concentration required for equivalent inhibitory activity by the Arg-Gly-Asp-(O-methyl-Tyr)-NH$_2$ of co-pending application Ser. No. 128,379.

DETAILED DESCRIPTION OF THE INVENTION

The novel platelet aggregation inhibitors of the present invention can be prepared by methods analogous to conventional peptide synthesis. Thus, a suitable method of synthesis is analogous to the soli phase synthesis of Merrifield, *J. Amer. Chem. Soc.* 85, 2149–2154 (1963); *Science* 150, 178–185 (1965); Ibid. 232, 341–347 (1986).

The solid phase synthesis provides a growing peptide chain anchored by its carboxyl terminus to a solid support, e.g., a resin such as chloromethylated polystyrene resin or p-methylbenzhydrylamine resin when synthesizing a peptide amide derivative. The use of various N-protecting groups, e.g. the carbobenzyloxy group, the t-butyloxycarbonyl group (BOC) or the N-(9-fluorenyl-methylcarbonyl) group (Fmoc), various coupling reagents, e.g., dicyclohexylcarbodiimide (DCC) or carbonyldiimidazole, various cleavage reagents, e.g., trifluoracetic acid (TFA) in methylene chloride ($CH_2Cl_2$) and other such reagents of classical solution phase peptide synthesis also are used in conventional solid phase synthesis of peptides.

In the present invention, aspartic acid is used as the C-terminal moiety of the peptide mimetic compound for initiating the solid phase synthesis, and protection is preferably carried out with Fmoc blocking reagents. The preferred solid phase resin is a Sasrin ® resin which is commercially available from Bachem Biosciences, Philadelphia, Pa., and Sigma Chemical Co., St. Louis, Mo. The Fmoc-O-t-butyl-L-aspartic acid is amidated with suitable aryl amine, for example, 4-methoxyphenylethylamine and, following removal of the t-butyl group, the product is attached to the solid phase resin. In a succeeding step, the Fmoc group is removed from the aspartic acid residue and the Fmoc protected aminoalkanoyl group is coupled thereto. Following removal of the latter Fmoc group, the amino group is guanidated and the resin is then cleaved off to yield the desired peptide mimetic product.

The following schematic outline illustrates the foregoing solid phase synthesis of the preferred 8-guanidino-octanoyl-Asp-2-(4-methoxyphenyl)-ethylamide.

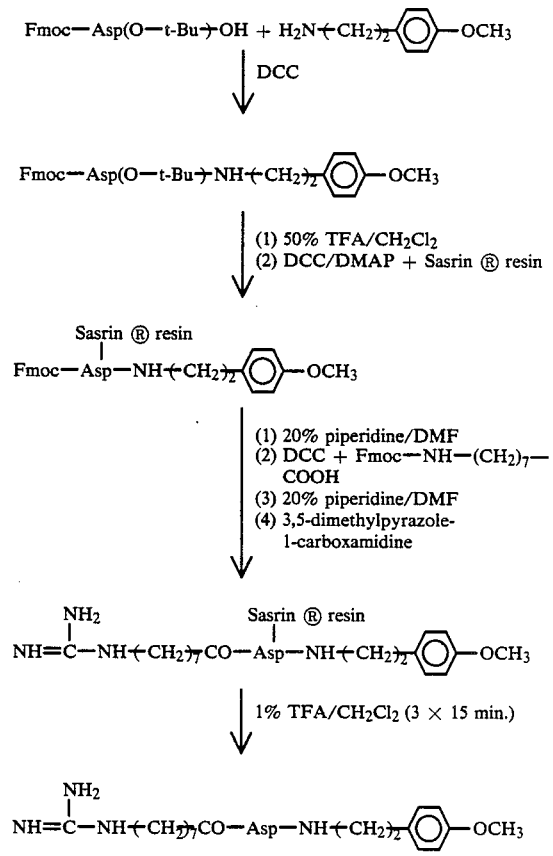

Another suitable method of synthesis of the platelet aggregation inhibitors of the present invention is a solution phase synthesis. This method can commence with the preparation of an aspartyl amide which is then coupled with a quanidino alkanoic acid as illustrated in the following schematic outline for the synthesis of 8-quanidino-octanoyl-Asp-2-(4-methoxyphenyl)-ethyl amide.

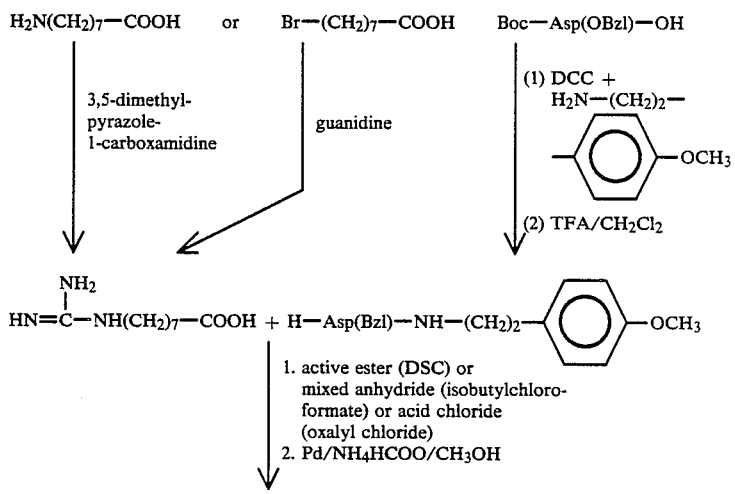

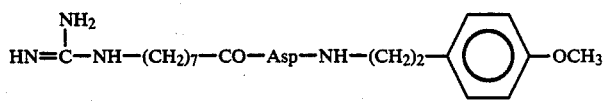

The platelet-binding inhibitor activity of the peptide mimetic compounds of this invention can be demonstrated by various assays. In one assay, platelet aggregation is examined in platelet-rich plasma which also is rich in fibrinogen and other plasma proteins. The % inhibition is determined for the test compound by comparing the extent of platelet aggregation in the presence and absence of the test compound.

In another test, the effect of the peptide mimetic compound on collagen induced thrombocytopenia (platelet aggregation) is measured in vivo in the rat. Again, the % inhibition is determined for the test compound and compared against a saine or ethanol vehicle in the absence of the test compound.

In these assays, the test compound results are then compared with the activity of the known active inhibitor tetrapeptide Arg-Gly-Asp-Ser.

Based on the test results obtained with these Compounds, it is believed that they will be useful in a variety of therapeutic interventions, for example, preventing re-occlusion following re-canalization procedures such as post fibrinolytic therapy, thrombolytic therapy, angioplasty and coronary bypass surgery. Other potential uses are for prevention of myocardial infarct, recurrent myocardial infarct, unstable angina, peripheral artery disease, cerebral ischemia, stroke and diseases of platelet hyperaggregability, and to prevent occlusion in hemodialysis, shunt procedures and to prevent progression of atherosclerosis.

The following examples will further illustrate the invention in greater detail although it will be appreciated that the invention is not limited to these specific examples.

EXAMPLE I

Solid Phase Synthesis of 8-guanidino-octanoyl-Asp-2-(4-methoxyphenyl)ethyl amide

A. Fmoc-Asp(OtBu)-2-(4-methoxyphenyl)ethyl amide

Fmoc-Asp(OtBu)-OH (32.6 g; 79.3 mmoles) was dissolved in $CH_2Cl_2$ and cooled in an ice bath. DCC (16.3 g; 79.3 mmoles) dissolved in minimum $CH_2Cl_2$ was added with stirring to the mixture. After 5 minutes stirring, 4-methoxyphenyl ethyl amine (10.0 g; 66.1 mmoles) was added dropwise. The mixture was stirred overnight and filtered. The filtrate was evaporated to dryness and the residue was dissolved in ethyl acetate and refrigerated. Additional solid was filtered and the filtrate was washed with saturated $NaHCO_3$ (3×) and with 0.1 N HCl (1×). The organic phase was dried over sodium sulfate, filtered and evaporated, and the residue was recrystallized from ethyl acetate/hexane.

The structure of the title compound was confirmed by FAB-MS.

B. Fmoc-Asp-2-(4-methoxyphenyl)ethyl amide

Fmoc-Asp(OtBu)-2-(4-methoxyphenyl)ethyl amide (5.44 g; 10 mmoles) was treated with 50% $TFA/CH_2Cl_2$ for 90 minutes at room temperature. The solvent was evaporated and the residue was triturated with ethyl ether/petroleum ether. The precipitate was dried and used without further purification.

C. 8-(Fmoc-amino)-octanoic acid

8-Amino-octanoic acid (3.98 g; 25 mmoles) was dissolved in saturated sodium carbonate and the solution was added to fluorenylmethyloxycarbonyl succinimide ester (8.4 g; 25 mmoles) dissolved in dioxane. The mixture was stirred overnight and the solvent was evaporated. The residue was redissolved in chloroform (200 ml) and washed with 0.5 N HCl (3×50 ml) and water (50 ml). The organic phase was dried over sodium sulfate, filtered and evaporated to dryness and the residue was recrystallized from ethyl acetate/petroleum ether. The yield was 12.8 g; FAB-MS: (M+H)=382.

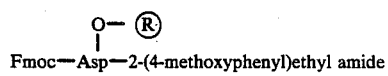

Fmoc—Asp—2-(4-methoxyphenyl)ethyl amide

D. Fmoc-Asp-2-(4-methoxyphenyl)ethyl amide

Fmoc-Asp-2-(4-methoxyphenyl)ethyl amide from B (8 mmoles) was coupled with Sasrin resin (7 g; 0.7 mmole OH/g resin) in N,N-dimethylformamide (DMF) (50 ml) with dicyclohexylcarbodiimide (8 mmoles) and 4-dimethylamino-pyridine (0.5 g). The reaction was carried out overnight after which the resin was washed with DMF (5×40 ml) and $CH_2Cl_2$ (2×20 ml). The substitution was found to be 0.326 mmole Asp/g resin by amino acid analysis.

E. 8-guanidino-octanoyl-Asp-2-(4-methoxyphenyl)ethyl amide

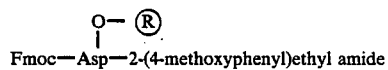

Fmoc—Asp—2-(4-methoxyphenyl)ethyl amide from D (3 g) was treated with 20% piperidine/DMF (3×5 min) and washed thoroughly with DMF (6×20 ml). 8-(Fmoc-amino)-octanoic acid (1.9 g; 5 mmoles) was then coupled to the resin overnight with dicyclohexylcarbodiimide (1.03 g; 5 mmoles) in $DMF/CH_2Cl_2$ (2:1; 20 ml). After several washes with DMF, the Fmoc group was removed with 20% piperidine/DMF as described above. The resin was reacted overnight with 3,5-dimethyl-pyrazole-1-carboxamidine (2.1 g; 10 mmoles) in DMF (40 ml), and the resin was washed with DMF (6×40 ml) and $CH_2Cl_2$ (2×40 ml). The product was cleaved from the resin using 2% $TFA/CH_2Cl_2$ (3×15 min) and was purified on a C-18 μBondapak reversed phase HPLC column (1.9 cm×15 cm). The compound was dissolved in 15% $CH_3CN$, applied to the column and eluted with 15% $CH_3CN/H_2O/0.5\%$ TFA at a flow rate of 9 ml/min.

EXAMPLE II

Solution Synthesis of 8-guanidino-octanoyl-Asp-2-(4-methoxyphenyl)ethyl amide

A. 8-guanidino-octanoic acid 3,5-dimethyl-pyrazole-1-carboxamidine (100 g; 0.5 Mole) and N,N-diisopropylethyl amine (DIEA) (65 g; 0.5 Mole) were suspended in dioxane (300 ml) and water (115 ml). 8-Amino-octanoic acid (48 g; 0.3 Mole) was added to the mixture with stirring. The colorless solution was then refluxed for 2 days. The product was filtered and washed with water (3×50 ml).

The dried material weighed 60 g; FAB-MS: (M+H)=202.

B. Boc-Asp(OBzl)-2-(4-methoxyphenyl)ethyl amide

Boc-Asp(OBzl)-OH (38.8 g; 0.12 Mole) was dissolved in $CH_2Cl_2$ (250 ml) and cooled in a dry ice/acetone bath. DCC (24.75 g; 0.12 Mole) dissolved in $CH_2Cl_2$ (50 ml) was added slowly. After stirring for 10 minutes 4-methoxyphenylethyl amine (15.1 g; 0.1 Mole) was added dropwise and stirring was continued for another hour at room temperature. The mixture was filtered and the filtrate was washed with saturated $NaHCO_3$ solution (×50 ml) and 1N HCl (50 ml). The organic phase was dried over sodium sulfate and evaporated to an oil. Yield: 41.5 g; FAB-MS: (M+Li)=463.

C. HCL.Asp(Obzl)-2-(4-methoxyphenyl)ethyl amide

Boc-Asp(OBzl)-2-(4-methoxyphenyl)ethyl amide from B (0.91 Mole) was treated with 4N HCl/dioxane (80 ml) for 1 hour. The solution was evaporated to an oil which was used in the next step without further purification.

D. 8-guanidino-octanoyl-Asp(OBzl)-2-(4-methoxyphenyl)-ethyl amide

8-Guanidino-octanoic acid HCl(0.11 Mole) was suspended in DMF (100 ml) and pyridine (20 ml). Disuccinimidyl dicarbonate (DSC) (25.6 g; 0.1 Mole) and 4-dimethyl-amino-pyridine (1 g) were added to the suspension, which became a clear solution after 15 minutes stirring. The mixture was stirred for 2 hours at which point HC.Asp(OBz)-2-(4-methoxyphenyl)ethyl amide from C and DIEA (12.9 g; 0.1 Mole) were added. The reaction was allowed to stir overnight after which it was evaporated to dryness.

E. 8-guanidino-octanoyl-Asp-2-(4-methoxyphenyl)ethyl amide

The crude product from D and ammonium formate (5 g) were dissolved in methanol (600 ml) and maintained under a nitrogen atmosphere. The solution was added slowly to 10% Pd/C (10 g) and the mixture was stirred overnight. The catalyst was removed by filtration and the filtrate was evaporated to an oil (200 ml). The crude produce was dissolved in 15% acetonitrile and purified on a C-18 μBondapak column (5 cm×30 cm; 15–20 μsilica) by eluting with a linear gradient of 1% A to 30% A that was started 10 minutes after injection of the compound onto the column. (A=100% $CH_3CN$/0.05% TFA; B=15% $CH_3CN/H_2O$/0.05% TFA).

EXAMPLE III

Solution Synthesis of 9-quanidino-nonanoyl-Asp-2-(4-methoxyphenyl)ethyl amide

A. Formation of free guanidine

Guanidine carbonate (11.41 g; 63.3 mmoles) was dissolved in 25 ml of water and sulfuric acid (3.52 m; 63.3 mmoles) and barium hydroxide (19.97 g; 63.3 mmoles) were added. The mixture was stirred and cooled on ice. The precipitate was removed by filtration or centrifugation and the solution containing the free guanidine was used directly in the next step.

B. Synthesis of 9-guanidino-nonanoic acid

9-Bromo-nonanoic acid (5 gm; 21.1 mmoles) was dissolved in dioxane (50 ml) and the free guanidine solution from A was added. The mixture was refluxed overnight, and the white precipitate was filtered and washed three times with cold water and then lyophilized from one equivalent of 0.5 M HCl. The yield was 2.77 g (85%) and the structure of the title compound was verified by FAB-MS, NMR, and elemental analysis.

C. Synthesis of 9-guanidino-nonanoyl-Asp-2-(4-methoxyphenyl)ethyl amide

Fmoc-Asp(OtBu)-2-(4-methoxyphenyl)ethyl amide (3 g; 5.5 mmoles, from I.A) was dissolved in 30 ml of 10% diethylamine/DMF to remove the Fmoc protecting group. The mixture was stirred for 1 hour and evaporated to dryness. 9-guanidino-nonanoic acid (1.54 g; 7.16 mmoles) was suspended in 10% pyridine/DMF and di-(N-succinimidyl) oxalate (2.44 g, 8.59 mmoles) and 4-dimethylamino-pyridine (0.5 g) were added to the suspension. After stirring for 1 hour, the mixture was added to the deprotected Asp(OtBu)-2-(4-methoxyphenyl)ethyl amide from above and stirred overnight. A white precipitate was filtered and the filtrate was evaporated to dryness. The resulting product was treated with 50% $TFA/CH_2Cl_2$ for 30 minutes to remove the t-butyl protection and crude product was obtained following evaporation. This crude material can be stored in a dessicator and was purified on a μBondapak C-18 column (1.9 cm×15 cm) with a linear gradient of 10–30% $CH_3CN/H_2O$.

Other illustrative peptide mimetic compounds of the invention as defined herein and prepared by methods analogous to the methods of Examples I to III, above, by substituting other suitable ω-amino alkanoic acids, e.g., 7-aminoheptanoic acid or 10-aminodecanoic acid, or ω-bromo alkanoic acids, e.g., 9-bromo nonanoic acid, for an equivalent amount of the 8-amino octanoic acid, and/or by substituting other suitable arylamines, e.g., 4-methoxybenzylamine, 2-(3,4-dimethoxyphenyl)ethylamine, naphthylethylamine or 2-thienylethylamine, for an equivalent amount of the 4-methoxyphenethylamine in said Examples. These illustrative peptide mimetic compounds are then tested in vitro for inhibition of ADP induced platelet aggregation in human platelet rich plasma (Example IV) and in vivo for inhibition of collagen induced rat thrombocytopenia (Example V). The compounds thus made and tested and their test results are set forth in Tables 1 and II following Examples IV and V, respectively.

EXAMPLE IV

In-Vitro Human Platelet Aggregation in PRP

Healthy male or female donors who have not taken any antiplatelet drugs for at least 2 weeks were fasted for 8 hours prior to drawing blood; then 30 ml whole blood was collected using a butterfly needle and 30 cc plastic syringe with 3 ml of 0.129 M buffered sodium citrate (3.8%). The syringe was rotated carefully as blood was drawn to mix the citrate. Platelet-rich plasma (PRP) was prepared by centrifugation at 100×g for 10 minutes at room temperature, allowing the centrifuge to coast to a stop without braking. The PRP was removed from the blood with a plastic pipette and placed in a plastic capped, 50 ml Corning conical sterile centrifuge tube which was held at room temperature. Platelet poor plasma (PPP) was prepared by centrifuging the remaining blood at 2000×g for 15 minutes at room temperature allowing the centrifuge to coast to a stop without braking. The PRP was adjusted with PPP to a count of 2–3×$10^8$ platelets per ml. 400 μl of the PRP preparation and 50 μl of the compound to be tested or saline were preincubated for 1 minute at 37° C. in a Payton aggregometer (Payton Scientific, Inc., Buffalo, N.Y.). 50 μl of adenosine 5'-diphosphate (ADP) (50 μM) was added to the cuvettes and the aggregation was monitored for 1 minute. All compounds are tested in duplicate. Results are calculated as follows: Percent of control=[(maximal OD minus initial OD of compound) divided by (maximal OD minus initial OD of control saline)]×100. The % inhibition=100−(percent of control).

The compounds tested and their activity results in % inhibition at $10^{-4}$ M and median inhibitory concentration (IC50) were as recorded in Table 1. IC50's (if a compound showed 50% inhibition) were calculated by linear regression of the dose response curve.

TABLE I

| INHIBITION OF ADP-INDUCED PLATELET AGGREGATION IN HUMAN PRP | | |
|---|---|---|
| COMPOUND | HUMAN PRP % INHIBITION AT $10^{-4}$ M | IC50 [M] |
| Arg—Gly—Asp—Ser | 25 | $1.3 \times 10^{-4}$ |
| Arg—Gly—Asp(O—methyl-Tyr)—NH2 | 100 | $3.0 \times 10^{-5}$ |
| 8-guanidino-octanoyl-Asp—2-(4-methoxyphenyl)-ethyl amide | 100 | $1.0 \times 1.0^{-5}$ |
| 8-guanidino-octanoyl-Asp—2-(3,4-dimethoxyphenyl)ethyl amide | 100 | $1.2 \times 10^{-5}$ |
| 8-guanidino-octanoyl-Asp—4-methoxybenzyl amide | 100 | $3.3 \times 10^{-5}$ |
| 8-guanidino-octanoyl-Asp—(4-phenyl)-phenylalanine amide | 100 | $1.7 \times 10^{-5}$ |
| 9-guanidino-nonanoyl-Asp—2-(4-methoxyphenyl)ethyl amide | 100 | $2.7 \times 10^{-5}$ |
| 10-guanidino-decanoyl-Asp—2-(4-methoxyphenyl)ethyl amide | 65 | $7.0 \times 10^{-5}$ |
| 7-guanidino-heptanoyl-Asp—2-(4-methoxyphenyl)ethyl amide | 43 | not tested |
| N—(4-guanidinobutyl)-Gly—Asp—2-(4-methoxyphenyl)ethyl amide | 0 | not tested |

EXAMPLE V

In Vivo Rat Thrombocytopenia

Male rats [Charles River, CRL:CD(SD), 400–450 g] were used. The rats were anesthetized with Na pentabarbital (65 mg/kg, Vet Labs, Limited, Inc., Lenexa, Kan.). Two incisions were made to expose both jugular veins. Using an infusion pump (Harvard Apparatus, South Natick, Mass.) and a 5 cc syringe with a 19 g. butterfly, the test compound or vehicle was infused into the left jugular vein at a rate of 0.39 ml/min for 3 min. After 2 min of compound/vehicle infusion, collagen (60 μg/kg) (Helena Laboratories, Beaumont, Tex.) was injected with a one ml syringe into the right jugular vein. The body cavity was opened and the vena cava was exposed for blood sampling. One min after the collagen injection, compound infusion was stopped and blood was sampled from the vena cava (within 30 sec) with a 3 cc syringe containing 0.3 mg of 4.5% EDTA/-Tris (0.1 M) (pH 7.35) plus 150 μM indomethacin. Platelet rich plasma (PRP) was prepared by centrifuging the blood at 126×g for 10 min. Five μl of PRP was counted in 20 ml of Isoton ®III in a Coulter Counter.

Percent inhibition of collagen induced aggregation was calculated by comparison of the platelet counts in animals that were treated with test compound and collagen (a) with platelet counts for animals receiving no collagen (non-aggregated control) and (b) with platelet counts for animals receiving vehicle and collagen (aggregated control).

The % inhibition of platelet aggregation in vivo and the median effective dose (ED50) of the test compounds are set forth in the following Table II.

TABLE II

| INHIBITION OF COLLAGEN INDUCED RAT THROMBOCYTOPENIA | | |
|---|---|---|
| COMPOUND | % INHIBITION AT 1 mg/kg | ED50 mg/kg |
| Arg—Gly—Asp—Ser | 22.85 | inactive |
| Arg—Gly—Asp—(O—methyl-Tyr)—NH2 | 74.60 | 0.87 |
| 8-guanidino-octanoyl-Asp-2-(4-methoxyphenyl)-ethyl amide | 67.05 | 0.07 |

The novel 8-guanidino-octanoyl-Asp-2-(4-methoxyphenyl)-ethyl amide also was found to be orally active in rats with an ED50 of 7.8 mg/Kg.

The novel peptide mimetic compounds of this invention can be used for administration to humans by conventional means, such as by parenteral or oral methods of administration, preferably in formulations with pharmaceutically acceptable diluents or carriers. The preferable route of administration as a platelet aggregation inhibitor is parenteral, especially intravenously. Intravenous administration of the peptide mimetic compounds in solution with normal physiological saline, human albumin and other such diluents and carriers is illustrative. Other suitable formulations of the active peptide mimetic compounds in pharmaceutically acceptable diluents and carriers in therapeutic dosage form can be prepared by reference to general texts in the pharmaceutical field such as, for example, *Remington's Pharmaceutical Sciences*, Ed. Arthur Osol, 16th ed., 1980, Mack Publishing Co., Easton, Pa.

Various other examples will be apparent to the person skilled in the art after reading the present disclosure without departing from the spirit and scope of the invention. It is intended that all such examples be included within the scope of the appended claims.

What is claimed is:

1. A peptide mimetic compound having the following chemical structure:

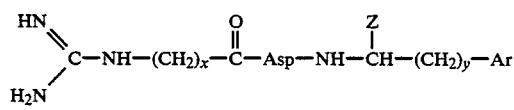

wherein
x=6 to 10,
y=0 to 4,
Z=H, COOH, $CONH_2$ or $C_{1-6}$alkyl,
Ar=phenyl, biphenyl or napthyl, each substituted with 1 to 3 methoxy groups, or an unsubstituted phenyl, biphenyl, napthyl, and
Asp=aspartic acid residue.

2. 8-guanidino-octanoyl-Asp-2-(4-methoxyphenyl)-ethyl amide.

3. 8-guanidino-octanoy-Asp-2-(3,4-dimethoxyphenyl)-ethyl amide.

4. 8-guanidino-octanoy-Asp-4-methoxybenzyl amide.

5. 8-guanidino-octanoyl-Asp-(4-phenyl)phenylalanine amide.

6. 9-guanidino-nonanoyl-Asp-2-(4-methoxypheny)-ethyl amide.

7. 10-guanidino-decanoyl-Asp-2-(4-methoxypheny)-ethyl amide.

8. 7-guanidino-heptanoyl-Asp-2-(4-methoxyphenyl)-ethyl amide.

9. The method of inhibiting platelet aggregation in a warm blooded mammal comprising administering to said mammal an effective amount of the peptide mimetic compound of claim 1 in a pharmaceutically acceptable carrier.

10. The method of inhibiting formation of a thrombus in a warm blooded mammal comprising administering to said mammal an effective amount of the peptide mimetic compound of claim 1 in a pharmaceutically acceptable carrier.